United States Patent [19]

Kühn et al.

[11] Patent Number: 5,041,204

[45] Date of Patent: Aug. 20, 1991

[54] ELECTROCHEMICAL MEASURING CELL FOR DETECTING HYDROGEN CYANIDE OR SULFUR DIOXIDE

[75] Inventors: Uwe Kühn, Wesenberg; Herbert Kiesele; Stephan Haupt, both of Lübeck, all of Fed. Rep. of Germany

[73] Assignee: Drägerwerk Aktiengesellschaft, Lubeck, Fed. Rep. of Germany

[21] Appl. No.: 543,436

[22] Filed: Jun. 26, 1990

[30] Foreign Application Priority Data

Jul. 18, 1989 [DE] Fed. Rep. of Germany ....... 3923717

[51] Int. Cl.$^5$ ............................................ G01N 27/40
[52] U.S. Cl. ............................... 204/415; 204/153.14; 204/153.17; 204/153.19
[58] Field of Search ..................... 204/153.14, 153.17, 204/153.19, 415

[56] References Cited

U.S. PATENT DOCUMENTS

| | | | |
|---|---|---|---|
| 3,795,589 | 3/1974 | Dahms | 204/415 |
| 4,169,779 | 10/1979 | Tataria et al. | 204/415 |
| 4,227,974 | 10/1980 | Petersen et al. | 204/419 |
| 4,521,290 | 6/1985 | Venkatasetty | 204/415 |
| 4,756,804 | 7/1988 | Driscoll et al. | 204/415 |

Primary Examiner—T. Tung
Attorney, Agent, or Firm—Walter Ottesen

[57] ABSTRACT

The invention is directed to an electrochemical measuring cell for detecting hydrogen cyanide or sulfur dioxide by means of at least one measuring electrode and a counter electrode disposed in an electrolyte. The electrolyte is accommodated in a measuring chamber closed off with respect to the ambient by a membrane permeable to the substance to be detected. This measuring cell is improved in that the long-term stability of the measuring signal is increased and a corrosion of the electrodes is prevented. For this purpose, the electrolyte in the electrolyte chamber contains an additive of copper salts for catalyzing the oxidation of the substance to be detected.

10 Claims, 1 Drawing Sheet

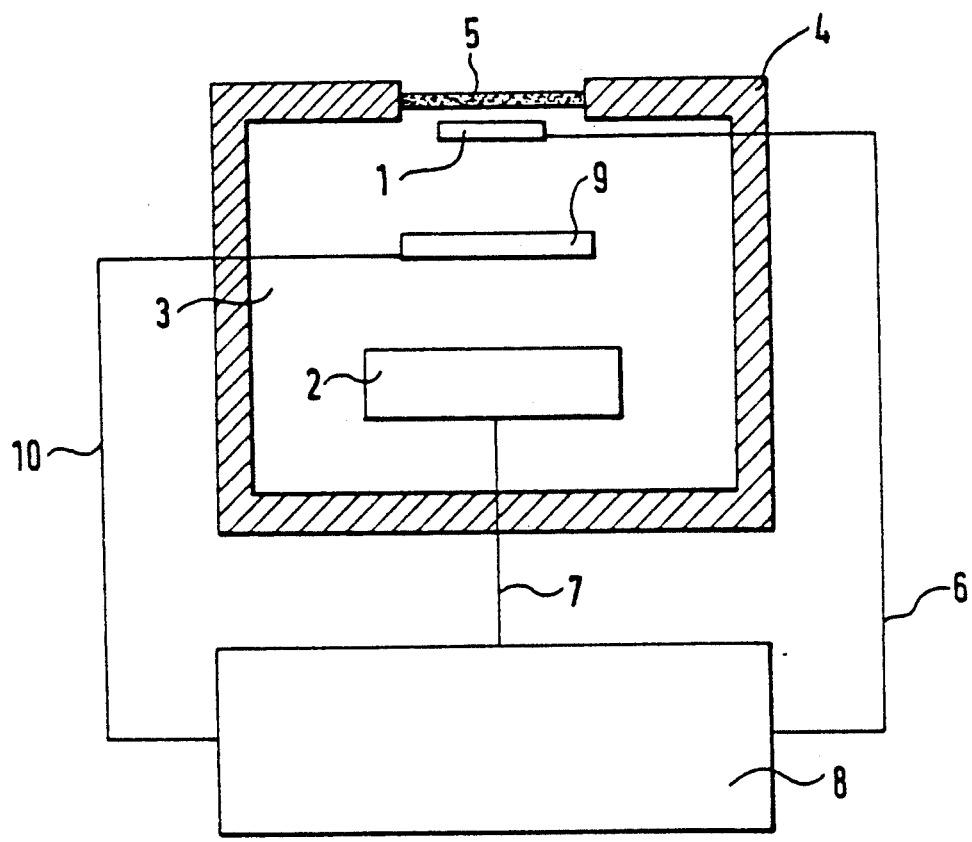

ELECTROCHEMICAL MEASURING CELL FOR DETECTING HYDROGEN CYANIDE OR SULFUR DIOXIDE

FIELD OF THE INVENTION

The invention relates to an electrochemical measuring cell for detecting hydrogen cyanide or sulfur dioxide by means of at least a measuring electrode and a counter electrode disposed in an electrolyte. The electrolyte is accommodated in a measuring chamber closed off with respect to the ambient by a membrane permeable to the substance to be detected.

BACKGROUND OF THE INVENTION

A measuring cell for detecting hydrogen cyanide is disclosed in U.S. Pat. No. 4,227,974.

In the known measuring arrangement, an Ag/Ag+ measuring electrode is utilized at which however hydrogen cyanide (HCN) reacts with the Ag+-ions present in solution to form a complex formation as represented by equations (1) and (2) below:

In this way, the electrochemical equilibrium is disturbed and the measuring electrode delivers Ag+-ions while partially decomposing until the equilibrium is restored as shown in equation (3). This condition produces electrode corrosion over a long term which influences the long-term stability of the measuring signal and leads to an undesired drift in the response of the measuring cell.

In view of the above, hydrogen cyanide is detected in known measuring cells in that the formed cyanide forms a complex with the dissolved silver ions thereby disturbing the electrode equilibrium so that the electrode must resupply Ag and consequently corrodes.

SUMMARY OF THE INVENTION

It is an object of the invention to provide a measuring cell of the kind described above which is improved so that the corrosion of the electrode material is avoided and the long-term stability of the measuring signal is increased.

The electrochemical measuring cell of the invention is for detecting a sample of hydrogen cyanide or sulfur dioxide. The measuring cell includes: a housing having an opening directed toward the ambient containing the sample to be detected and defining an electrolyte chamber; an electrolyte contained in the chamber; a membrane permeable to the sample and mounted on the housing for closing off the chamber with respect to the ambient; a measuring electrode and a counter electrode disposed in the chamber so as to be in spaced relationship to each other; and, the electrolyte containing an additive of copper salts for catalyzing the oxidation of the sample to be detected.

Thus, according to a feature of the invention, the electrolyte contains an additive of copper salts for catalyzing the oxidation of the substance to be detected.

The advantage of the invention is seen essentially in that the copper catalyst now makes possible the direct anode oxidation of the cyanide to cyanogen without the electrode participating in this chemical reaction mechanism so that the decomposition of electrode material is prevented. By means of the copper additive, the detection reaction takes place as an oxidation with only the dissolved copper participating with the HCN in the solution and with the actual measuring or working electrode now only producing the electrical contact to the electrolyte solution and thereby regenerating the copper catalyst. In this way, a liquid electrode for the reaction of the hydrogen cyanide is provided to a certain degree. The course of the reaction can be illustrated with the following individual steps:

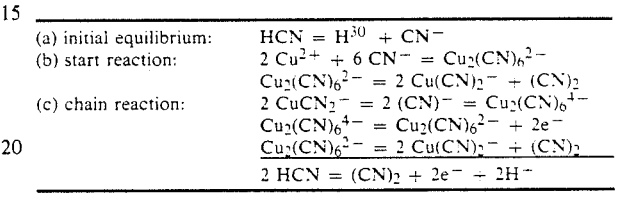

which is the result of the chain reaction.

A chain reaction is described in the article entitled "Formation Constant of the Tetracyanocuprate(II) Ion and the Mechanism of Its Decomposition" of Katagiri et al in the Journal of Inorganic Chemistry, Volume 20, pages 4143 to 4147, (1981). From this chain reaction, it is evident that cyanide can be oxidized to cyanogen with the participation of the copper salt as a catalyst without an electrode constituent being required therefor. One electron is released for each converted cyanide. The formation of a complex between hydrogen cyanide and an electrode constituent does not take place since the detection reaction takes place completely in the electrolyte solution.

An analogous situation can be found with the detection of sulfur dioxide where a sulfite ($SO_2^{2-}$ is present in lieu of the cyanide. A corresponding chain reaction is also described in the article entitled "Kinetics of the Electro-Oxidation of Sulfite Catalyzed by Copper Ion" by Katagiri et al in the Journal of the Electrochemical Society, Volume 136, No. 1, pages 101 to 108, (January 1989).

With the invention, an electrochemical measuring cell for detecting not only hydrogen cyanide, but also sulfur dioxide is realized because the added copper catalyst offers a selective gain with respect to the detection of hydrogen cyanide and sulfur dioxide because of the chain reaction present in the electrolyte. In addition, the detection sensitivity for the substances HCN and $SO_2$ as well as the resistance to contamination of the measuring cell is increased since now the entire two-phase boundary "electrolyte/gas" is able to trap the substance to be detected and to make the substance accessible for measurement and no longer only the three-phase boundary "electrode/electrolyte/gas".

The selection of a suitable electrode material, electrolyte and copper salt, is within the purview of those skilled with respect to the electrochemical compatibility of the components with respect to each other and familiar with the measurement requirements. An especially suitable selection for an electrolyte is sulfuric acid with an additive of copper(II)sulfate. A further suitable electrolyte is calcium nitrate with an additive of copper nitrate. If sulfuric acid is selected as the electrolyte, then the advantage is realized that disturbing secondary products are made harmless. These secondary products are formed from the dissolved HCN via hydrolysis or protonation.

An especially advantageous composition of the electrolyte is seen in that an additive of preferably $10^{-2}$ molar copper sulfate is added to a 4 molar sulfuric acid. The advantageous concentration range of the copper sulfate extends from $10^{-1}$ to $10^{-3}$ M.

It is especially advantageous to make the measuring and counter electrodes of gold in order to obtain the following: a large resistance to corrosion of the electrodes with reference to the electrolyte, a reduction in the cross-sensitivity to hydrogen and the capability of driving the measuring cell at an electrode voltage of 0 volts. The operation at 0 volts makes it possible to store the measuring cell in short circuit operation so that it can be immediately transferred to operational readiness when required. The residual current is then still further reduced and its dependency upon the ambient temperature is compensated at the same time.

BRIEF DESCRIPTION OF THE DRAWINGS

The invention will now be described with reference to the single FIGURE of the drawing which is a side elevation view, in section, of a measuring cell according to an embodiment of the invention.

DESCRIPTION OF THE PREFERRED EMBODIMENTS OF THE INVENTION

Referring to the drawing, the measuring cell is identified by reference numeral 1 and includes a counter electrode 2 and a reference electrode 9 all made of gold. The electrodes are introduced into an electrolyte chamber 3 of the measuring cell housing 4. The electrolyte chamber 3 is filled with an aqueous solution of 4 molar sulfuric acid with an additive of $10^{-2}$ molar copper sulfate.

The ambient contains the measuring sample with hydrogen cyanide or sulfur dioxide and the electrolyte chamber 3 is closed off with respect to the ambient by a membrane 5 permeable to hydrogen cyanide or sulfur dioxide. The measuring electrode 1, the counter electrode 2 and the reference electrode 9 are provided with respective measuring leads (6, 7, 10) which are led through the housing 4 and are connected to an evaluation unit 8 for further processing of the measuring signal.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for detecting a sample of hydrogen cyanide or sulfur dioxide, the measuring cell comprising:
    a housing having an opening directed toward the ambient containing the sample to be detected and defining an electrolyte chamber;
    an electrolyte contained in said chamber;
    a membrane permeable to said sample and mounted on said housing for closing off said chamber with respect to the ambient;
    a measuring electrode and a counter electrode disposed in said chamber so as to be in spaced relationship to each other;
    said measuring electrode and said counter electrode both being made of gold; and,
    said electrolyte containing copper salt for catalyzing the oxidation of the sample to be detected.

2. The electrochemical measuring cell of claim 1, wherein said copper salt is copper(II)sulfate and said electrolyte is aqueous sulfuric acid.

3. The electrochemical measuring cell of claim 2, wherein $10^{-1}$ to $10^{-3}$ molar copper(II)sulfate is added to 4 molar aqueous sulfuric acid.

4. The electrochemical measuring cell of claim 3, wherein $10^{-2}$ molar copper(II)sulfate is added to 4 molar aqueous sulfuric acid.

5. The electrochemical measuring cell of claim 2, wherein said cell is stored in short circuit operation so that said cell can be immediately transferred to operational readiness when required.

6. The electrochemical measuring cell of claim 1, further comprising a reference electrode arranged in said chamber and interposed between said measuring electrode and said counter electrode.

7. The electrochemical measuring cell of claim 6, wherein said reference electrodes is made of gold.

8. The electrochemical measuring cell of claim 1, wherein said cell is stored in short circuit operation so that said cell can be immediately transferred to operational readiness when required.

9. The electrochemical measuring cell of claim 8, said electrolyte being aqueous sulfuric acid.

10. The electrochemical measuring cell of claim 1, said electrolyte being aqueous sulfuric acid.

* * * * *

UNITED STATES PATENT AND TRADEMARK OFFICE
CERTIFICATE OF CORRECTION

PATENT NO. : 5,041,204
DATED : August 20, 1991
INVENTOR(S) : Uwe Kühn, Herbert Kiesele and Stephan Haupt It is certified that error appears in the above-identified patent and that said Letters Patent is hereby corrected as shown below:

In column 1, line 43: delete "Ag" and substitute -- $Ag^+$ -- therefor.

In column 2, line 16 (top line of table): delete "$H^{30}$" and substitute -- $H^+$ -- therefor.

In column 2, line 39: delete "$(SO_2$" and substitute -- $(SO_3)^{2-}$ -- therefor.

In column 3, line 8: delete "M" and substitute -- molar -- therefor.

In column 4, line 40: delete "electrodes" and substitute -- electrode -- therefor.

Signed and Sealed this

Sixth Day of October, 1992

Attest:

DOUGLAS B. COMER

*Attesting Officer*  *Acting Commissioner of Patents and Trademarks*